United States Patent [19]

Klug

[11] Patent Number: 5,133,923
[45] Date of Patent: Jul. 28, 1992

[54] METHOD OF SIMULTANEOUSLY FORMING CONTAINER STRAP HOLDERS ON URINARY LATEX CONTAINERS

[75] Inventor: K. Robert P. Klug, Tucson, Ariz.

[73] Assignee: Sierra Laboratories, Inc., Tucson, Ariz.

[21] Appl. No.: 808,735

[22] Filed: Dec. 17, 1991

Related U.S. Application Data

[62] Division of Ser. No. 695,903, May 6, 1991.

[51] Int. Cl.⁵ .......................... B28B 1/38; B28B 7/28; B28B 21/46
[52] U.S. Cl. .................... 264/303; 264/306; 425/275
[58] Field of Search ............. 264/301, 303, 306; 425/269, 270, 272, 274, 275

[56] References Cited

U.S. PATENT DOCUMENTS

| | | | |
|---|---|---|---|
| 2,119,496 | 5/1938 | Spanel | 425/275 |
| 2,264,154 | 11/1941 | Spanel | 425/269 |
| 2,810,928 | 10/1957 | Raiche | 425/269 |
| 4,846,816 | 7/1989 | Manfredi | 604/323 |
| 4,976,816 | 11/1990 | Coye | 425/269 |

Primary Examiner—Jan H. Silbaugh
Assistant Examiner—A. Ortiz
Attorney, Agent, or Firm—Victor Flores

[57] ABSTRACT

A latex container, and associated former and method for producing, for use as a leg bag by urinary incontinent males. The latex leg bag is provided with strap holders that are integrally formed simultaneously with the leg bag structure to provide a more structurally reliable strap holder. The strap holder includes a nodal growth of latex, simultaneously grown during the a latex coagulation process, that bridges an interstice on the former to close the strap holder loop. The leg bag container is provided having a skewed entry neck for facilitating better dressing of the delivery tube during use, and a concave shape to better conform to the user's leg. The former is machined with corresponding structure to form the leg bag in a latex coagulation process.

1 Claim, 2 Drawing Sheets

METHOD OF SIMULTANEOUSLY FORMING CONTAINER STRAP HOLDERS ON URINARY LATEX CONTAINERS

This is a divisional of application Ser. No. 07/695,903, filed May 6, 1991.

FIELD OF THE INVENTION

The present invention relates to latex container apparatus and associated strap holders and methods of forming. More particularly, the present invention relates to latex urinary bags and strap securing means provided with the bag structure for attachment to a users leg. More particularly, the present invention relates to latex urinary bags of the type having strap holding means that are considered integral with the latex bag body structure.

DESCRIPTION OF THE PRIOR ART

Latex leg bags are used by male incontinent to control urinary discharge. The nonporous characteristic of latex results in its wide use for producing leg bags for the male incontinent. The elongated portion of the bag is generally attached to the leg of the individual at the thigh or calf areas using the bag's strap holders and attachment strapping.

The latex leg bags are typically formed using aluminum formers having a flat oval shape that produce similarly shaped bags. Although concave shapes are desirable for better conformity to a user's leg, the flat shapes have been accepted for use in that the pliable nature of the latex material can generally be relied upon for conforming the flat pliable bag structure to the person's leg area. In attaching the bag, a user also relies upon the straps holders provided on the bag, in combination with auxilliary straps that encircle the leg, for supporting the bag while being used.

Presently known, and commercially available leg bags provide entry and drain necks that are straight and oppose each other and are in substantial alignment with the central axis of the elongated bag portion. The entry neck port houses associated check valve and tubing that is detachably connected to the male user's penis. Although the straight orientation of the entry neck with respect to the drain neck port has been accepted by the user, a skewed orientation with respect to the central axis of the elongated bag is preferred because such orientation results in facilitating a more natural placement of the interconnecting tubing and also avoids tube kinking.

The strap holders provided on leg bags have been traditionally provided on the bag by bonding latex strips to the bag using adhesives. The adhesive bond has not proven reliable during the life of the latex bag, notwithstanding the special manufacturing effort involved in effecting the bonding of the latex strips. Improvements in providing the strap holders as integral holding straps are taught in U.S. Pat. No. 4,976,816 wherein two semi-cured latex components, namely a preformed strap holder strip and the latex bag, are affixed together. The two surfaces are wetted with uncured latex prior to mating the surfaces and held together using mechanical jigs during the curing process. Although referred to as integral holding straps, the body structures of the holding strap, the corresponding portion of the bag and the connecting joint are formed at separate times and are not believed to be an integral holding strap. The manufacturing steps in producing two separate latex components and the manipulation procedures to effect the latex joint between the holding straps and the bag are viewed as a cost disadvantages. The integral holding strap as taught by U.S. Pat. No. 4,976,816 lacks the simultaneity in formation to effect a more structurally reliable strap holder.

Therefore, a need is seen to exist for an improved container for use as a leg bag by urinary incontinent male.

More particularly, a need is seen to exist for an improved container for use as a leg bag by a urinary incontinent male that is provided with strap holders that are formed simultaneously with the leg bag structure to provide a more structurally reliable strap holder.

Even more particularly, a need is seen to exist for an improved container for use as a leg bag by a urinary incontinent male that is provided with strap holders that are formed simultaneously with the leg bag structure and that is also provided, having a skewed entry neck for providing better delivery tube dressing and a concave shape to better conform to the user's leg.

A related need is seen to exist for a mold/former and method for producing the above needed latex container.

SUMMARY OF THE INVENTION

Accordingly, the primary object of the present invention is to provide a latex container having strap holders means that are formed simultaneously with the leg bag structure.

A closely related object of the present invention is to provide a mold, referred to hereinafter as a former, having structure for producing the latex container.

Another related object of the present invention is to provide a method for using the former in a latex coagulation process for producing the latex container.

Another object of the present invention is to provide a latex bag container having a skewed entry neck for facilitating better dressing of the delivery tube and also having a concave shape to better conform to the user's leg.

The foregoing objects are accomplished by providing an aluminum former for being dipped into a latex emulsion for forming the latex container. The aluminum former includes a body portion, for forming an elongated bag portion, at least one protruding machined portion, for forming at least one strap holder, and an interstice portion provided at a distal end of the at least one protruding machined portion that facilitates formation of a latex nodal growth during the latex coagulation process. The elongated bag portion and the at least one strap holder being a uniform simultaneous formation up to an end portion defined by the distal end of the protruding portion. The machined interstice portion provided at the distal end the protruding machined portion facilitates the formation of a latex nodal growth during the latex coagulation process that bridges the end of the strap holder back to the elongated bag portion. The strap holder and an opposing portion of the elongated bag delineate a slot for receiving a support strap used to attach to a user's leg. The former may include several of the protruding portions to produce as many of the strap holder as are deemed necessary. It has been determined that an upper and lower set of two laterally opposed strap holders are adequate to support the bag. Further, the former end that defines the entry neck of the bag apparatus may be machined to provide a skewed potion that will form a similarly skewed entry neck for facilitating better dressing of the delivery tube. Also, the former may be provided having a concave shape for producing the leg bag having a concave shape to better conform to the user's leg.

Therefore, to the accomplishments of the foregoing objects, the invention consists of the foregoing features hereinafter fully described and particularly pointed out in the claims, the accompanying drawings and the following disclosure describing in detail the invention, such drawings and disclosure illustrating but one of the various ways in which the invention may be practiced.

DESCRIPTION OF THE PREFERRED EMBODIMENT

Figures 1, 2, 3:
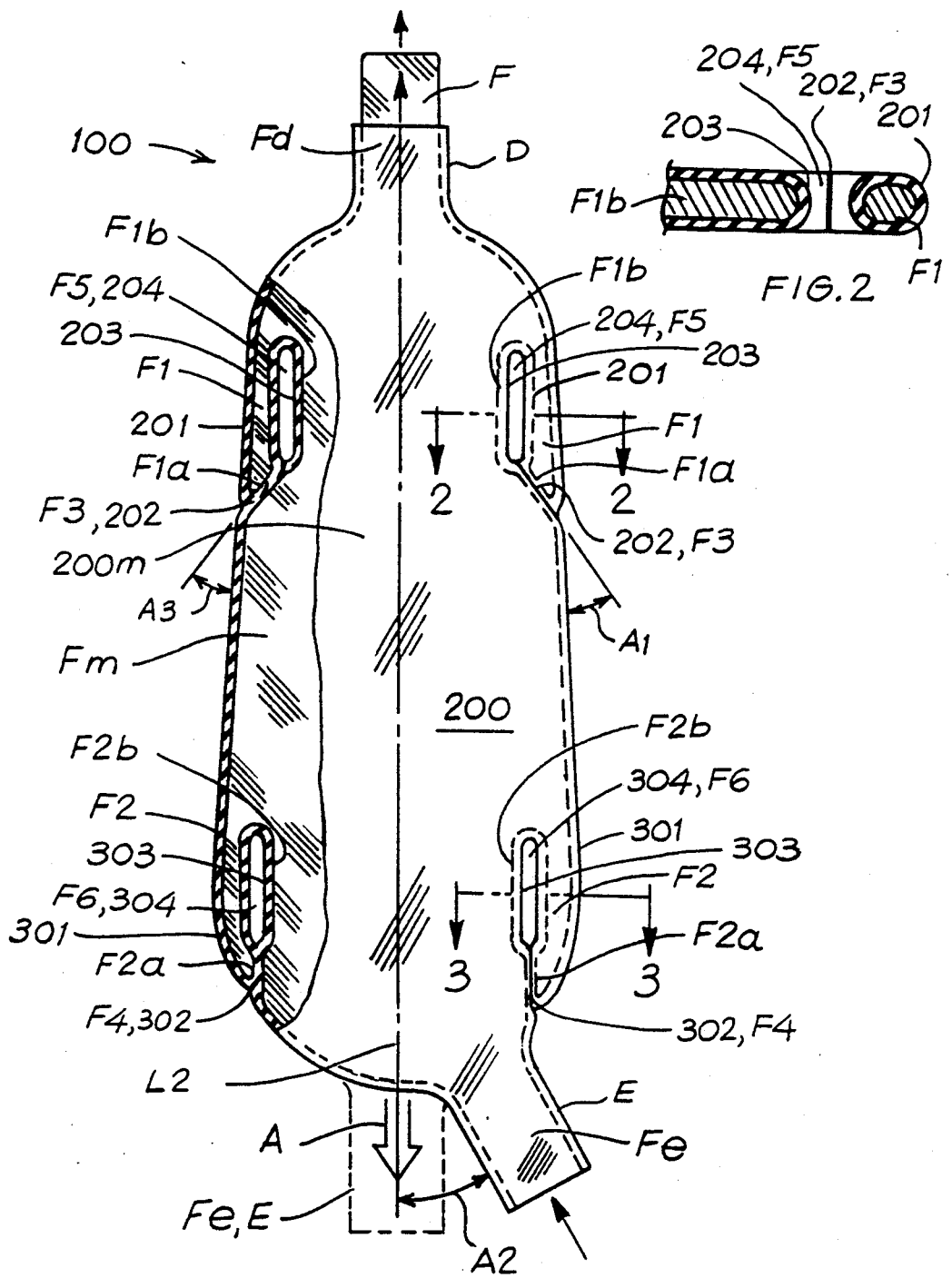
FIG. 1 is a partially cutaway plan view of a flat structured leg bag (container) according to the present invention shown in a formed state with the former (mold) used to produce it in a latex coagulation process.
FIG. 2 is cross-sectional view of the former and corresponding strap holder portion at the leg bag's drain-end taken along line 2—2 in FIG. 1.
FIG. 3 is cross-sectional view of the former and corresponding entry-neck-end, strap holder portion taken along line 3—3 in FIG. 1.

In accordance with the objects of the present invention, FIG. 1 depicts a combined apparatus 100 showing the former (mold) F and the leg bag 200 formed thereon. The former F comprises a main body portion Fm for forming the main elongated bag portion 200m. The former also comprises laterally opposed and longitudinally spaced protruding machined portion F1, F2 for forming, similarly located, strap holder formations 201, 301. Former F is machined having interstice portions F3, F4 at a distal ends F1a, F2a of protruding portions F1,F2 that facilitate formation of latex nodal growths 202, 302 during a latex coagulation process that forms bag 200. Protruding portions F1,F2, in combination with opposing former portions F1b, F2b and interstice portions F3, F4, delineate openings F5,F6. Similarly, strap holder formations 201,301, in combination with corresponding opposing portions 203,303, of said main elongated bag portion 200m, and nodal growths 202,302, delineate openings 204, 304 for receiving attachment straps S (see FIG. 4). Former F includes an entry neck portion Fe machined skewed at an angle A2 with respect to central longitudinal axis line L2 to form a similarly skewed bag entry neck E. The orientation of former entry neck portion Fe and bag entry neck E may also be provided as shown in alignment with line L2 and directly opposite the former drain neck portion Fd and the bag's drain neck D. The bag 200 is removable from former F in the direction as shown by arrow A. To facilitate this removal, the entry neck-end set of laterally spaced and opposing interstices F4 and nodal growths 302 are oriented substantially parallel with longitudinal axis line L2 while the drain-end set of laterally spaced and opposing interstices F3 and nodal growths 202 are skewed at angles A1 and A3 from longitudinal axis line L2.

As illustrated in cross section in FIGS. 2 and 3, the formation of leg bag 200 onto former F that occurs during the latex coagulation process results in simultaneous formation of opposing portions 203,303 onto former portion F1b, F2b, strap holders 201, 301 onto protruding machined portion F1,F2 and formation of nodal growths 202, 302 in interstices F3,F4. The formation results formation of loop opening 204,304 congruent with former openings F5,F6.

Figure 4:
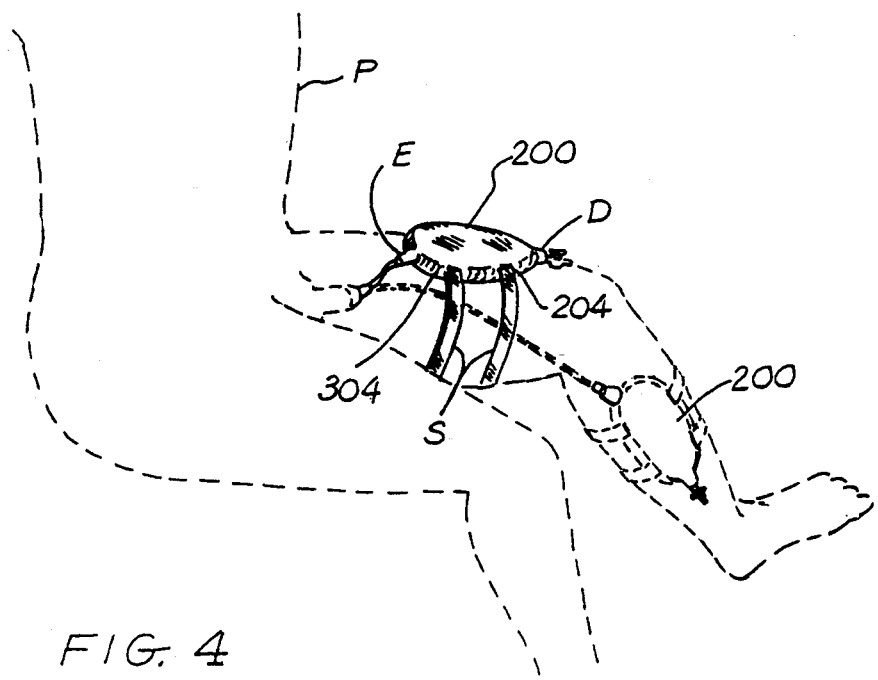
FIG. 4 is an application view of the present invention showing the latex container (leg bag) and strap holders attached to a male user at two possible leg locations.

FIG. 4 show a person P in a sitting position with the leg bag 200 according to the present invention attached to the left thigh using a pair of straps S looped through openings 204,304. FIG. 4 also shows leg bag 200 apparatus worn in an alternative position about the left calf of person P.

Figure 5:
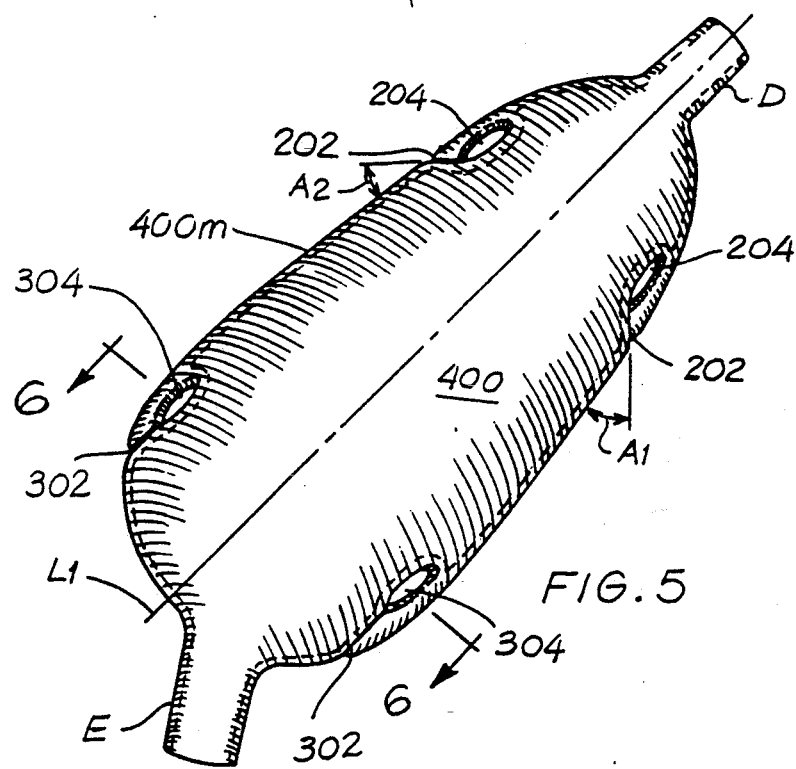
FIG. 5 is a plan view of a concave latex container according to the present invention illustrating the skewed entry neck and opposing sets of laterally spaced strap holders that were simultaneously formed with the illustrated leg bag.

FIG. 5 shows a curved leg bag 400 formed using a similarly shaped former F. Leg bag 400 is provided such that its concave portion will conform to the shape of a leg of the wearer. Aside from the concave structure, leg bag 400 comprises all of the features of leg bag 200 illustrated in FIG. 1, namely skewed entry neck E, nodal growths 302 in substantial parallel relationship with longitudinal axis line L1, strap holder openings 304, skewed nodal growths 202 and strap holder openings 204, all aspects being uniformly formed, including drain neck D.

Figure 6:
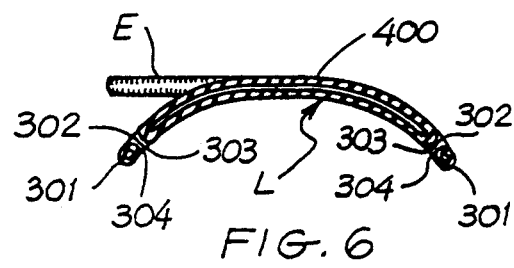
FIG. 6 is a cross-sectional view of the leg bag taken along line 6—6 in FIG. 5 illustrating the concave leg bag structure, the skewed entry neck port and the laterally opposed strap holders, including the nodal growth and slot portions.

FIG. 6 shows a cross-sectional view taken along line 6—6 in FIG. 5 and illustrates the uniformity of the simultaneous formation of the leg bag 400, preferably from latex material L, and further illustrates the elements of the invention, including the laterally opposing strap holders 301, openings 304, nodal growths 302, and opposing elongated body portions 303.

While, the art of forming leg bags is well known, the formation of leg bags according to the present eliminates the need for ancillary jigs, and associated costs, in that only one former F is required to produce a leg bag the accomplishes the total need of urinary incontinent male, preferably a former F that produces bag 400 although a flat shaped former F is not objectionable. Accordingly, the steps required to produce a leg bag 200, 400 according to the present invention include: (a) providing an aluminum dipping former F (mold), former F having at least one protruding machined portion F1,F2 for forming at least one strap holder 201,301 and also having a corresponding machined interstice portion F3,F4 provided at a distal end F1a,F2a of said at least one protruding machined portion F1,F2 for facilitating formation of nodal growths 202,302 during a coagulation process of latex that forms the latex leg bag; (b) providing an alcohol coagulant solution for dipping said former F in preparation for dipping into a latex emulsion; (c) providing a latex emulsion; (d) dipping said prepared former F into the latex emulsion to begin the coagulation process; (e) forming the latex leg bag, including simultaneously forming an elongated bag portion 200m, 400m, at least one strap holder 201,301 on said at least one protruding machined portion F1, F2 and said nodal growth 202,302 by coagulation buildup during said coagulation process until interstice F3, F4 is bridged; and (f) curing and removing said formed latex leg bag 200, 400 from said former F.

Therefore, while the present invention has been shown and described herein in what is believed to be the most practical and preferred embodiments, it is recognized that departures can be made therefrom within the scope of the invention, which scope is therefore not to be limited to the details disclosed therein but is to be accorded the full scope of the claims so as to embrace any and all equivalent apparatus.

I claim:

1. A method of forming a latex container said method comprising the steps of:
   (a) providing a former body for being dipped into latex emulsion for forming said latex container, said former body having at least one protruding machined portion delineating a former slot and an adjoining machined interstice portion extending outwardly towards an outer periphery of said former, said former slot facilitating formation of at least one strap holder slot, and said interstic portion facilitating formation of a solid nodal growth portion within said interstice portion during a coagulation process of said latex emulsion;
   (b) providing an alcohol coagulant solution and treating said former body with said solution in preparation for dipping in a latex emulsion;
   (c) providing said latex emulsion;
   (d) dipping said treated former body in said latex emulsion to begin said coagulation process;
   (e) forming said latex container on said former body including, simultaneously forming an elongated bag portion, forming said at least one strap holder slot about said former slot, and forming said solid nodal growth portion at said interstice portion by coagulation buildup of said latex emulsuion during said coagulation process until said interstice portion is bridged; and
   (f) curing and removing said formed latex container from said former.

* * * * *